(12) United States Patent
Chadwick

(10) Patent No.: US 10,188,176 B2
(45) Date of Patent: Jan. 29, 2019

(54) CLASP FOR SECURING FLEXIBLE BANDS

(71) Applicant: Endur ID, Inc., Hampton, NH (US)

(72) Inventor: Robert Chadwick, Hampton Falls, NH (US)

(73) Assignee: ENDUR ID, Hampton, NH (US)

( * ) Notice: Subject to any disclaimer, the term of this patent is extended or adjusted under 35 U.S.C. 154(b) by 155 days.

(21) Appl. No.: 15/097,556

(22) Filed: Apr. 13, 2016

(65) Prior Publication Data

US 2016/0219987 A1   Aug. 4, 2016

Related U.S. Application Data

(63) Continuation of application No. 13/656,206, filed on Oct. 19, 2012, now Pat. No. 9,339,408.

(60) Provisional application No. 61/550,152, filed on Oct. 21, 2011.

(51) Int. Cl.
| | |
|---|---|
| *A44B 11/10* | (2006.01) |
| *A61F 5/37* | (2006.01) |
| *A44B 11/06* | (2006.01) |
| *G09F 3/00* | (2006.01) |
| *B65B 61/20* | (2006.01) |
| *A44B 11/25* | (2006.01) |

(52) U.S. Cl.
CPC .............. *A44B 11/10* (2013.01); *A44B 11/06* (2013.01); *A44B 11/25* (2013.01); *A61F 5/3776* (2013.01); *B65B 61/202* (2013.01); *G09F 3/005* (2013.01); *Y10T 24/45194* (2015.01); *Y10T 29/4995* (2015.01)

(58) Field of Classification Search
CPC .......... A44B 11/10; A44B 11/06; A44B 11/25
See application file for complete search history.

(56) References Cited

U.S. PATENT DOCUMENTS

| | | | |
|---|---|---|---|
| 2,586,758 A | | 2/1952 | Zerr |
| 3,935,977 A | | 2/1976 | Bonnett |
| 4,049,357 A | * | 9/1977 | Hamisch, Jr. ........... F16G 11/02 16/444 |
| 4,416,038 A | | 11/1983 | Morrone, III |
| 4,635,698 A | * | 1/1987 | Anderson ............... E06B 9/326 160/178.2 |
| 5,208,950 A | * | 5/1993 | Merritt .................... F16G 11/14 24/115 H |
| 5,381,617 A | | 1/1995 | Schwartztol et al. |
| 5,473,797 A | * | 12/1995 | Wu ........................ E06B 9/326 160/178.1 R |
| 5,495,644 A | | 3/1996 | Mesher et al. |

(Continued)

OTHER PUBLICATIONS

Canadian Office Action dated Mar. 10, 2014, issued in corresponding Canadian Application No. 2,673,171.

*Primary Examiner* — Victor D Batson
*Assistant Examiner* — Matthew J Sullivan
(74) *Attorney, Agent, or Firm* — Onello & Mello, LLP

(57) ABSTRACT

A clasp is configured to permanently interlock around a flexible strip of material and includes first and second interlocking members. Each interlocking member includes two hooks and two recesses. Each of the hooks of the first side are arranged to engage and interlock with one of the recesses of the second side and each of the hooks of the second side are arranged to interlock with one of the recesses of the first side, so as to prevent movement between the interlocking members when interlocked.

19 Claims, 20 Drawing Sheets

(56) References Cited

U.S. PATENT DOCUMENTS

| | | | |
|---|---|---|---|
| 5,548,878 A | 8/1996 | Romagnoli | |
| 5,577,395 A | 11/1996 | Kuykendall | |
| 5,671,508 A | 9/1997 | Murai | |
| 5,689,860 A * | 11/1997 | Matoba | F16G 11/101 24/115 F |
| 6,453,519 B1 * | 9/2002 | Gelardi | A44B 11/06 24/16 PB |
| 6,510,592 B1 * | 1/2003 | Hamilton | A44B 11/06 24/170 |
| 6,571,434 B2 | 6/2003 | Ortiz | |
| 6,618,910 B1 * | 9/2003 | Pontaoe | F16G 11/14 24/115 H |
| 7,237,307 B2 | 7/2007 | Feschuk | |
| 7,367,092 B1 * | 5/2008 | Dilday | A44B 11/25 24/587.12 |
| 7,406,789 B2 | 8/2008 | Story | |
| 9,339,408 B2 * | 5/2016 | Chadwick | A61F 5/3776 |
| 2002/0088095 A1 * | 7/2002 | Hahn | B60R 16/0215 24/115 A |
| 2003/0217441 A1 * | 11/2003 | Eaton | A44B 11/25 24/115 F |
| 2005/0091801 A1 * | 5/2005 | Feschuk | F16G 11/14 24/115 R |
| 2005/0166436 A1 | 8/2005 | Girvin et al. | |
| 2006/0042151 A1 * | 3/2006 | Kavanaugh | A01K 91/03 43/44.89 |
| 2006/0196016 A1 * | 9/2006 | Cai | F16G 11/106 24/136 R |
| 2009/0255101 A1 | 10/2009 | Lin | |
| 2013/0091668 A1 * | 4/2013 | Turdjian | A44B 11/06 24/579.11 |
| 2015/0128384 A1 * | 5/2015 | Breen, IV | B65D 63/1063 24/16 PB |
| 2016/0088905 A1 * | 3/2016 | Perry | A44B 11/2596 2/338 |
| 2016/0157564 A1 * | 6/2016 | Howell | A44B 11/25 24/586.1 |

\* cited by examiner

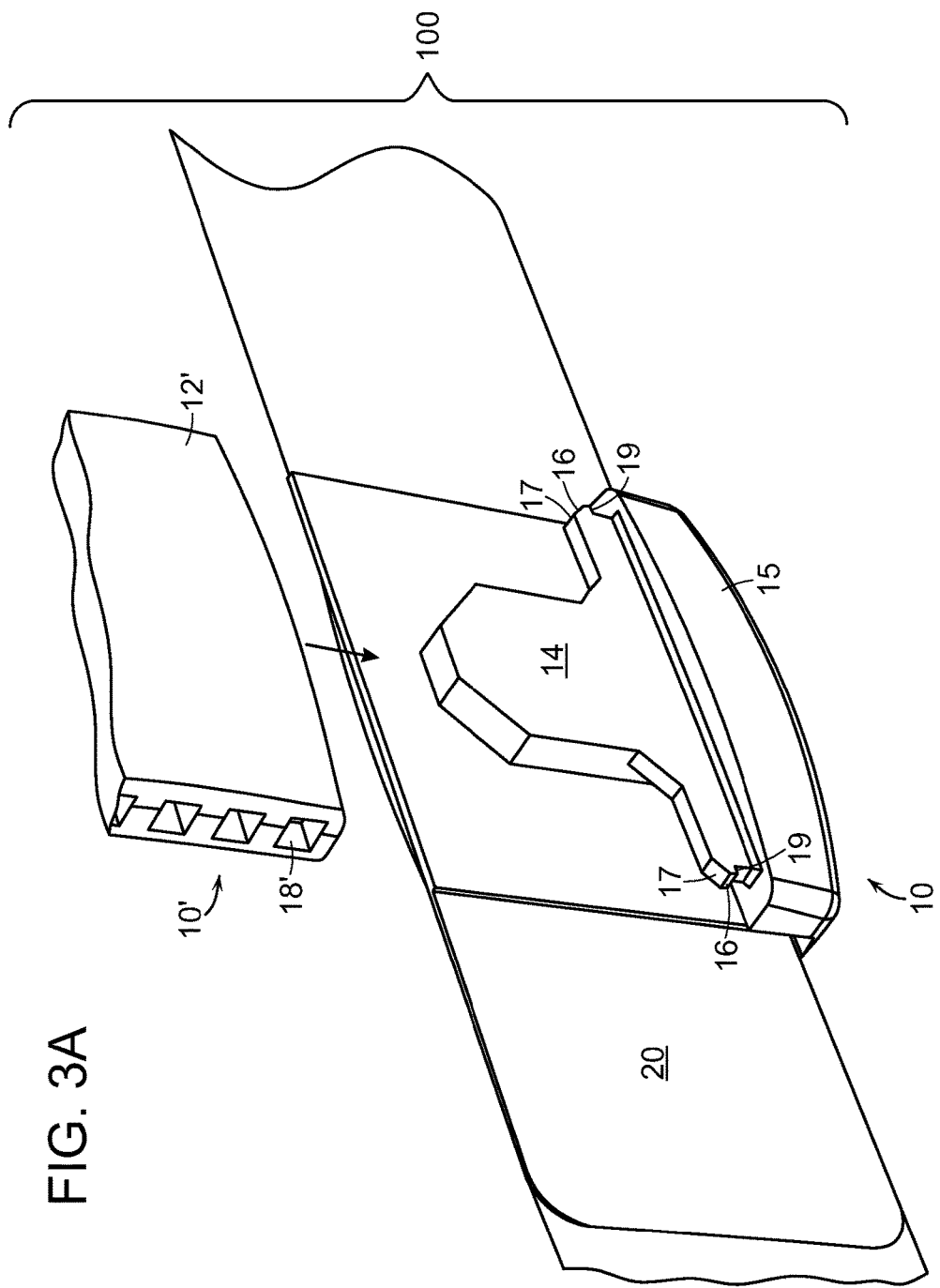

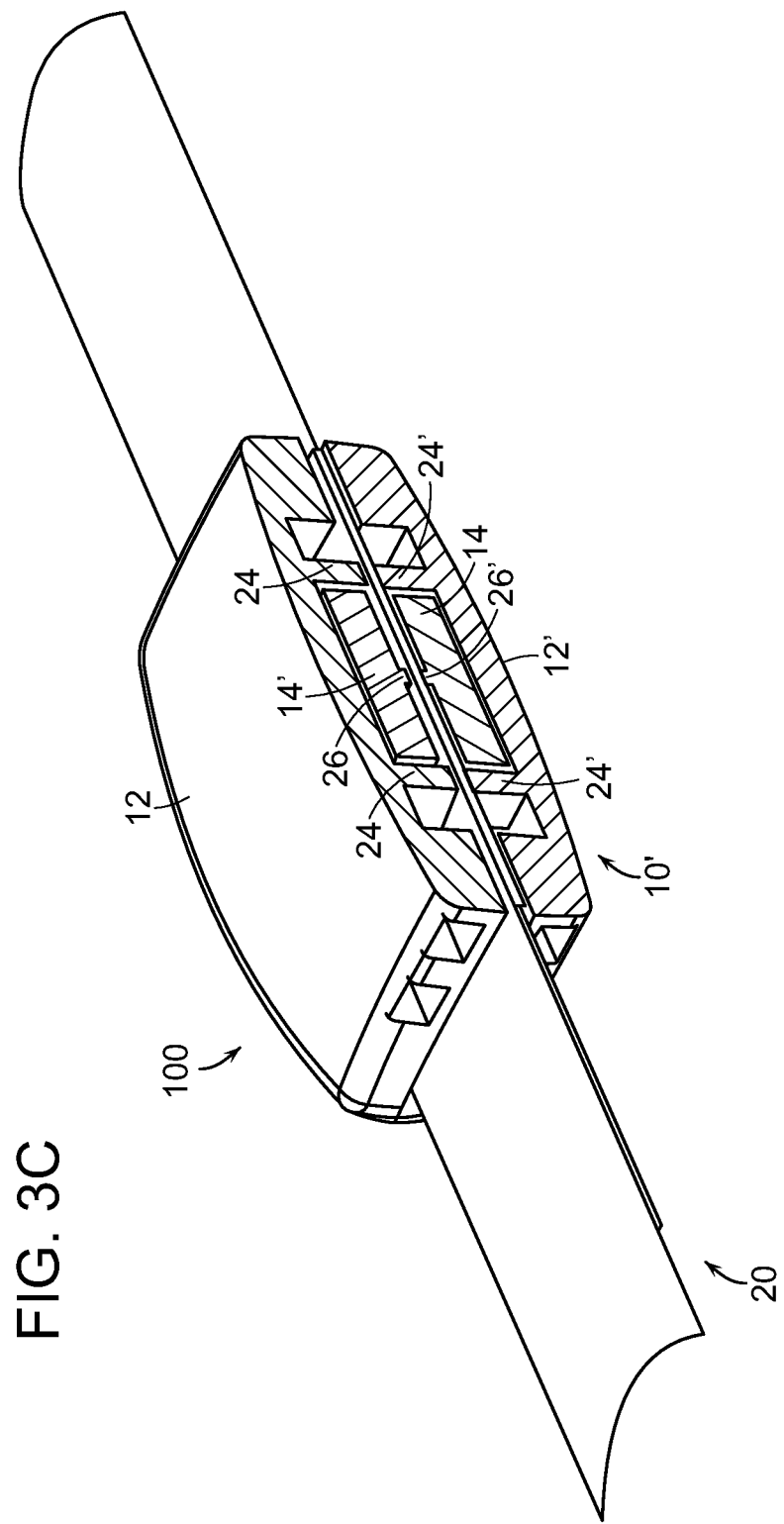

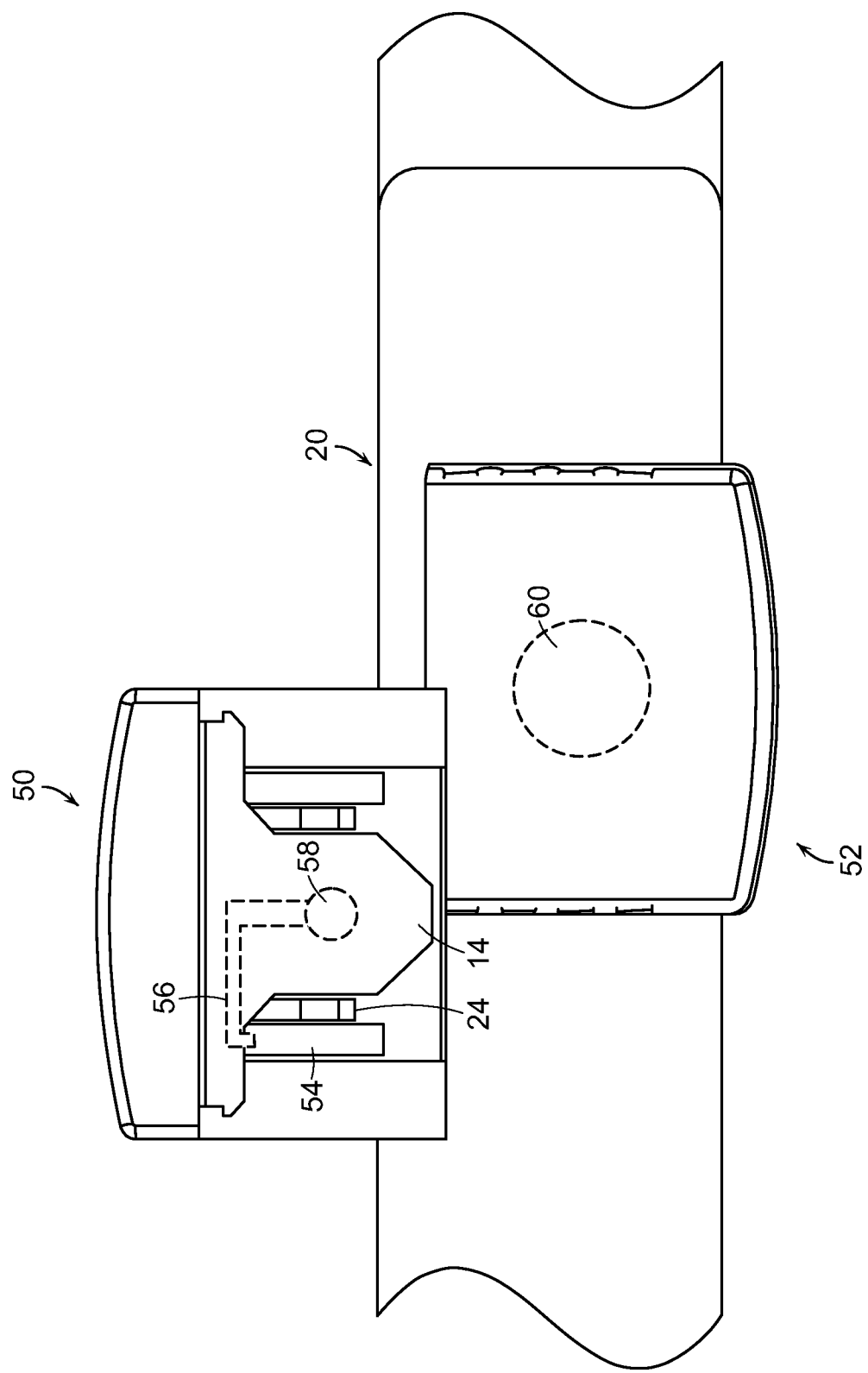

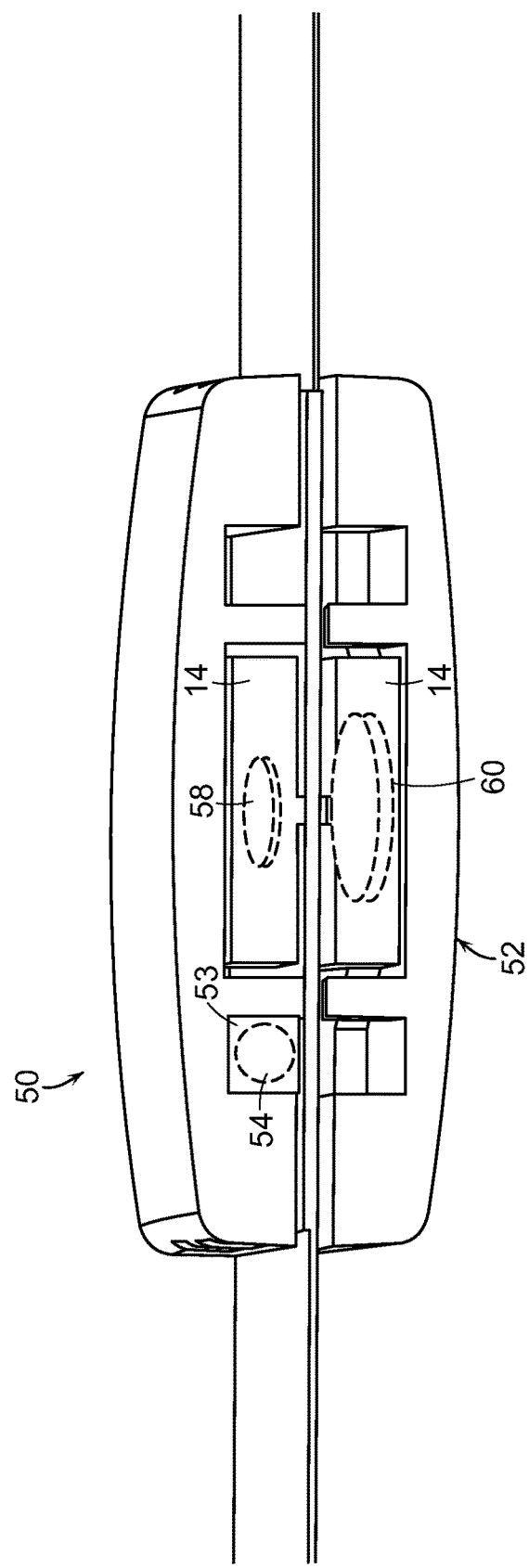

CLASP FOR SECURING FLEXIBLE BANDS

RELATED APPLICATIONS

This application is a continuation application of U.S. Ser. No. 13/656,206, filed on Oct. 19, 2012, which claims the benefit of U.S. Provisional Application No. 61/550,152, filed Oct. 21, 2011, the content of which is incorporated herein by reference in its entirety.

This application is related to U.S. Provisional Patent Application No. 61/182,881 filed on Jun. 1, 2001, U.S. patent application Ser. No. 12/766,451 filed on filed Apr. 23, 2010, published as U.S. Patent Application Publication No. 2011/0000113 A1, and U.S. patent application Ser. No. 12/766,451 filed on Apr. Jun. 17, 2009, published as U.S. Patent Application Publication No. 2010/0011643 A1, the contents of each of which are herein incorporated by reference in its entirety.

FIELD

Embodiments of inventive concepts relate to clasps for securing flexible bands, such as identification bands, and their methods of use and manufacture.

BACKGROUND

Flexible bands including, for example, wrist straps and bundled fiber/cable ribbons, can be exposed to external factors which compromise their connecting ends. For example, an identifying wrist strap on a patient is generally attached at its ends with an adhesive portion or unsecure interlocking feature, and the removal of the band at the resulting seam can be caused by accidental or intentional dismantling by the patient or others.

SUMMARY

As used herein, the terms "band" and "flexible band" may refer to any of the various flexible materials disclosed herein, or other flexible materials not specifically mentioned herein.

A clasp or closure is provided for enclosing/protecting a flexible band and, in an example embodiment, for securing the connecting ends of one or more bands. Some example embodiments provide identical mechanically interlocking members of a clasp that can be placed around a portion of a strap, including the connected ends (or seam) of one or more bands. The clasp may be configured to prevent slippage of the strap(s) within the clasp and protect an enclosed seam, for example, from being disconnected by external factors, such as a wearer of a band.

According to one aspect of the inventive concepts, a clasp is configured to permanently interlock around a flexible strip of material. In one example embodiment, the clasp includes first and second interlocking members, each interlocking member including two hooks and two recesses, each of the hooks of the first member arranged to engage and interlock with one of the recesses of the second member and each of the hooks of the second member arranged to interlock with one of the recesses of the first member, so as to prevent movement between the interlocking members when interlocked. When interlocked, the clasp may also prevent movement or slippage of the flexible strip of material.

According to another aspect of the inventive concepts, a clasp is provided that is configured to permanently interlock around a flexible strip of material. In one example embodiment, the clasp includes first and second interlocking members, each interlocking member including an outer shell having interlocking recesses formed therein, a tongue having interlocking hooks, and a tongue receiving slot formed between the tongue and the outer shell, wherein, when the first and second interlocking members are interlocked, the tongue of one interlocking member fits within the tongue receiving slot of the other interlocking member and the hooks of one interlocking member engage the interlocking recesses of the other interlocking member, thereby preventing disengagement of the interlocking members.

In some example embodiments, the first and second interlocking members are identically formed pieces.

In some example embodiments, the interlocking members are arranged so that, once engaged and interlocked, the clasp is permanently closed.

In some example embodiments, the clasp includes an inner surface forming a portion of the tongue receiving slot, including internal ribs protruding from the inner surface and forming opposing sides of the tongue receiving slot.

In some example embodiments, the tongues are arranged so that when the first and second interlocking members are interlocked, they define a path configured to compress and secure the flexible strip to substantially prevent movement within the clasp.

In some example embodiments, the tongues further include protrusions extending from a tongue inner surface forming a portion of the tongue receiving slot, the protrusions configured to substantially prevent sliding of the flexible strip between the interlocking members when interlocked.

In some example embodiments, each interlocking member further includes a base from which the outer shell and tongue extend substantially in parallel.

In some example embodiments, the tongue of each interlocking member is configured to slidably engage the tongue receiving slot of the other interlocking member.

In some example embodiments, when the first and second interlocking members are interlocked, a portion of the flexible strip of material is disposed between and in parallel with the tongues and outer shells of the first and second interlocking members.

In some example embodiments, the clasp is arranged to enclose and prevent access to a seam of the flexible strip of material. In some embodiments, the flexible strip of material is a flexible wrist strap or band.

In some example embodiments, the strip of material comprises at least one of a strip of cables, plastic, and fibers.

In some example embodiments, the clasp is constructed substantially of plastic, resin and/or metal.

In some example embodiments, each interlocking hook comprises an angled member configured to facilitate insertion into a corresponding interlocking recess and a stop member configured to prohibit removal of the interlocking hook from the corresponding interlocking recess.

An interlocking member, comprising a shell including a base, a tongue extending from the base, a tongue receiving slot defined between the tongue and the shell, and a positive interlocking mechanism and a negative interlocking mechanism. The interlocking member is configured to interlock with a second interlocking member to form a clasp configured to permanently secure a flexible band.

According to another aspect of the inventive concepts, a method of enclosing and protecting a flexible strip of material is provided, the method including enclosing the flexible strip of material within a clasp. In an embodiment, enclosing the flexible strip of material within a clasp includes engaging and interlocking first and second members of the clasp about the flexible strip of material, the engaging and interlocking of the first and second members including interlocking two hooks of the first member with two corresponding recesses of the second member and engaging and interlocking two hooks of the second member with two corresponding recesses of the first member.

According to another aspect of the inventive concepts, a method of permanently securing a flexible strip of material is provided. The method includes providing a clasp comprising first and second interlocking members. In an embodiment, each interlocking member includes an outer shell having interlocking recesses formed therein and a tongue having interlocking hooks, and a tongue receiving slot formed between the tongue and the outer shell. In an embodiment, the method includes disposing a portion of the flexible strip of material within the tongue receiving slot of the first interlocking member and interlocking the second interlocking member with the first interlocking member, including positioning the tongue of one interlocking member within the tongue receiving slot of the other interlocking member and forcing the hooks of one interlocking member within the interlocking recesses of the other interlocking member, so as to prevent disengagement of the interlocking members.

In accordance with some aspects of the inventive concepts, provided is a method of permanently securing a flexible band. The method comprises providing a clasp comprising first and second interlocking members. Each interlocking member comprises a shell including a base, a tongue extending from the base, a tongue receiving slot defined between the tongue and the shell, and a positive interlocking mechanism and a negative interlocking mechanism. The method further comprises disposing a flexible band in a channel passing through the tongue receiving slot of the first interlocking member and permanently combining the second interlocking member with the first interlocking member.

In some example embodiments, the first and second interlocking members are identically formed pieces.

In some example embodiments, the interlocking members are engaged and interlocked to permanently close the clasp.

In some example embodiments, interlocking the first and second members of the clasp about the flexible strip of material substantially prevents slippage of the flexible strip of material within the clasp.

In some example embodiments, the method includes enclosing a seam of the flexible strip of material within the clasp by interlocking the first and second members of the clasp about the connecting portions of the flexible strip of material. In some embodiments, the flexible strip of material is a wrist or ankle band.

In some example embodiments, positioning the tongue of one interlocking member within the tongue receiving slot of the other interlocking member includes slidably engaging the tongue of each interlocking member into the tongue receiving slot of the other interlocking member.

In some example embodiments, each interlocking member further includes a base from which the outer shell and tongue extend substantially in parallel.

In some example embodiments, interlocking the first and second interlocking members includes irremovably securing a portion of the flexible strip of material between and in parallel with the tongues and outer shells of the first and second interlocking members.

In some example embodiments, the tongues further comprise protrusions extending from a tongue inner surface forming a portion of the tongue receiving slot, the protrusions configured to reduce sliding of the flexible strip between the interlocking members when interlocked.

In some example embodiments, each outer shell includes an inner surface forming a portion of the tongue receiving slot, including internal ribs protruding from the inner surface and forming opposing sides of the tongue receiving slot.

In some example embodiments, when the first and second interlocking members are interlocked, they define a path configured to compress and secure the flexible strip to substantially prevent movement within the clasp.

BRIEF DESCRIPTION OF THE DRAWINGS

The foregoing and other features and advantages of embodiments of the present inventive concepts will be apparent from the more particular description of embodiments of the inventive concepts, as illustrated in the accompanying drawings in which like reference characters refer to the same elements throughout the different views. The drawings are not necessarily to scale, emphasis instead being placed upon illustrating the principles of the inventive concepts in the drawings.

FIG. 2B shows a top view of the interlocking member of FIG. 2A and FIG. 2C shows a side view of the interlocking member of FIG. 2A, according to an example embodiment of the inventive concepts.

FIGS. 3A and 3B are illustrative perspective views of a clasp comprising two interlocking members, according to an example embodiment of the present inventive concepts. FIG. 3C is a cross-sectional perspective view of the clasp of FIG. 3B taken along line A-A', according to an example embodiment of the present inventive concepts.

FIGS. 6A and 7A are illustrative perspective views of two interlocking members of a clasp incorporating an active RFID chip, according to an example embodiment of the inventive concepts. FIGS. 6B and 7B are cross-sectional perspective views of the interlocking members of FIGS. 6A and 7A forming part of a clasp that is cut along line A-A' as in FIG. 3A, respectively, according to an example embodiment of the inventive concepts.

DETAILED DESCRIPTION

Figure 1A:
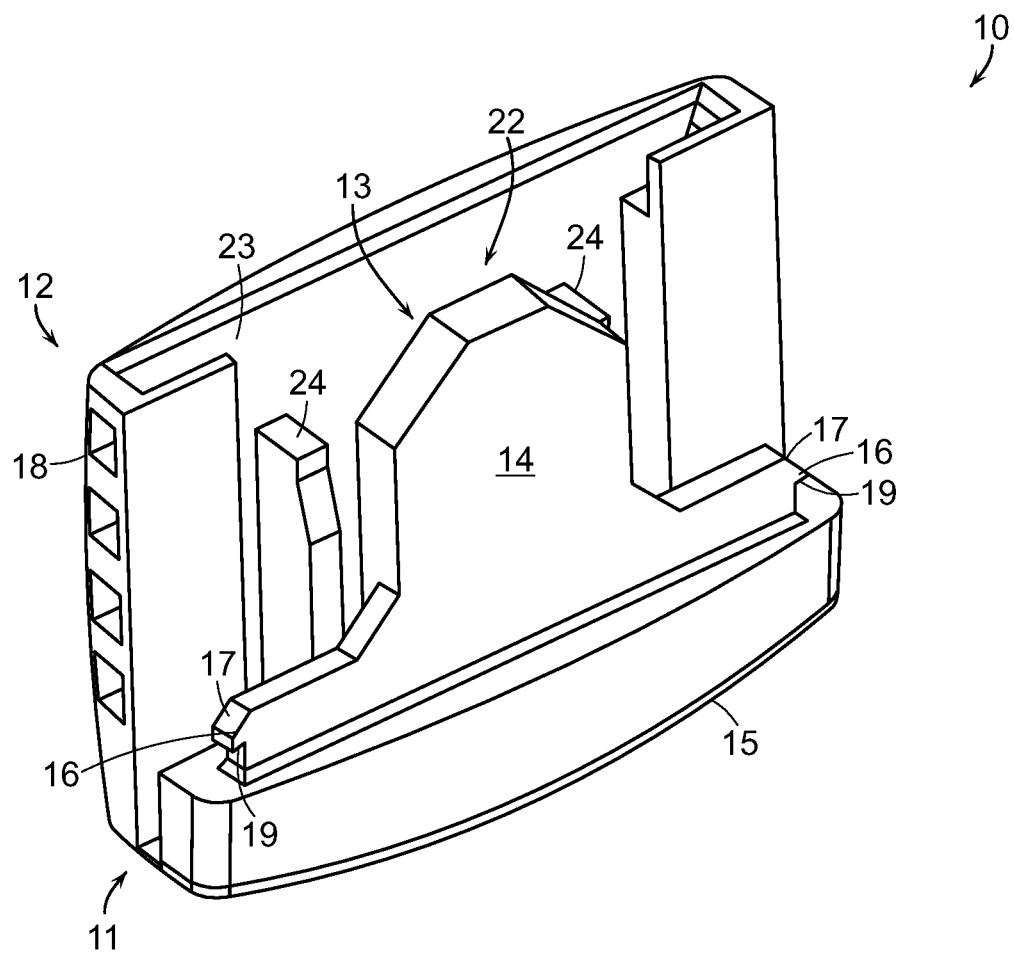
FIGS. 1A through 1C are illustrative perspective views of an interlocking member, as one of two interlocking members used to form a clasp, according to an example embodiment of the inventive concepts.

The foregoing and other objects, features and advantages of the embodiments of inventive concepts will be apparent from the more particular description of embodiments of inventive concepts, as illustrated in the accompanying drawings. The drawings are not necessarily to scale, emphasis instead being placed upon illustrating the principles of the inventive concept in the drawings.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

In accordance with various aspects of the inventive concepts, provided is a clasp that may be used with any number of flexible bands, such as standard polyester identification bands of products. The clasp may be used with various types of identification bands, straps, bracelets, anklets, or the like. The clasp may be used in various types of settings, medical facilities (for example, hospitals), nursing homes, paid entrance venues (for example, clubs, concerts, sporting events, museums), schools and universities, member only venues, and secure locations, as examples. The clasp may add an additional layer of security for use in facilities where the subject may not cooperate, for example. Examples of such facilities include: mental health facilities, lock-up facilities, detention centers and prisons.

The clasp may be used, as an example, with straps or wrist bands that include Valéron® Strength Films, which is a flexible cross laminated high strength polyethylene film. The cross laminated high strength polyethylene film may be treated with polyester on both sides to protect the strap from heat. A coating on the cross laminated high strength polyethylene film may be water proof and scratch proof in order to protect the information stored on the strap.

In example embodiments, the clasp is easy to use, able to be put on a strap or wrist band without the use of tools, very difficult or substantially impossible to open without tools or breakage, and not able to be used as a weapon. It also is, preferably, comfortable and unobtrusive when worn The clasp described herein may be used to bind any two flat ribbon like materials without any destruction of the bound materials. For example, the clasp described herein may bind two ribbons containing fiber optics without destroying the integrity of the optics within.

Other possible applications of the example embodiments include providing clasps for security seals for trucking, rails and containers. In one example embodiment, the clasps may be used for labels for shipping containers. In another example embodiment, the clasps may be used to attach ribbons to packages. In another example embodiment, the clasps may be used to create a belt or to cinch clothing.

In various embodiments, the clasp of the present invention includes two substantially identical interlocking members that connect to secure and enclose a portion of a strap, band, ribbon or wrist band. In such cases, any two interlocking members can be used such that the user need not be concerned with getting two different parts.

In an example embodiment, the clasp uses four positive latching mechanisms, each of two interlocking members having two male and two female mechanisms configured to engage with the corresponding mechanisms of the other interlocking member. A positively locked and secure clasp may be provided with the application of some physical force that forces each male mechanism into the corresponding female mechanism as the two interlocking members are pressed together to form a clasp. That is, no tools are required to connect the two interlocking members. In addition, an example embodiment of the clasp is designed to be a single use device, so no provision is made to disengage it once locked. This provides security as it cannot be removed by any party.

The clasp of the example embodiments of the present inventive concepts when used with ID bands (for example, patient or inmate ID bands), as an example, may cover adhesive flaps on the band and make them inaccessible to the wearer. The clasp is positioned as to cover the flaps, as the two interlocking members are locked together; internal ribs engage the band and lock the clasp into that position so that the clasp cannot be slid sideways to gain access to the bands adhesive flaps. In this manner, a seam of a band may be secured within the clasp.

To ease alignment when affixing the clasp to the strap or band, internal alignment pins guide the two interlocking members into place, making it easy to apply the clasp.

Figure 1B:
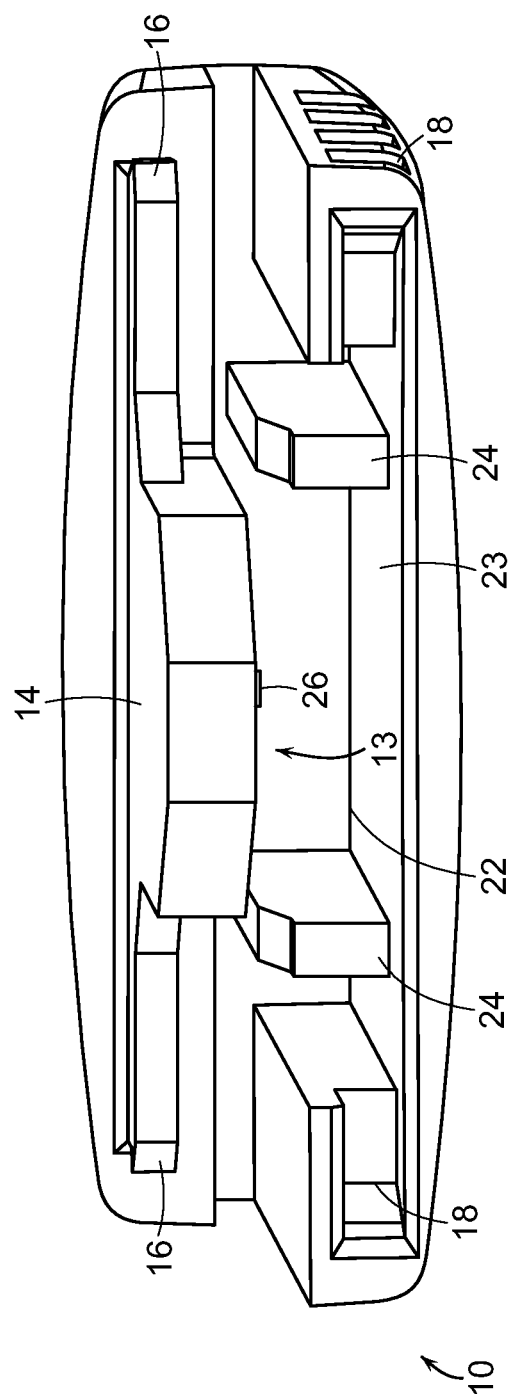
Figure 1C:
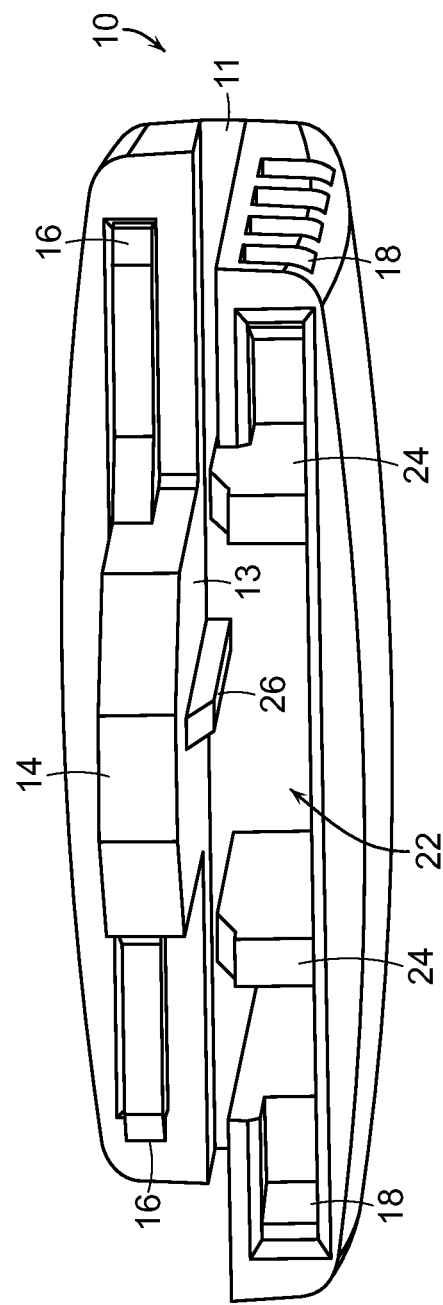
Figure 1D:
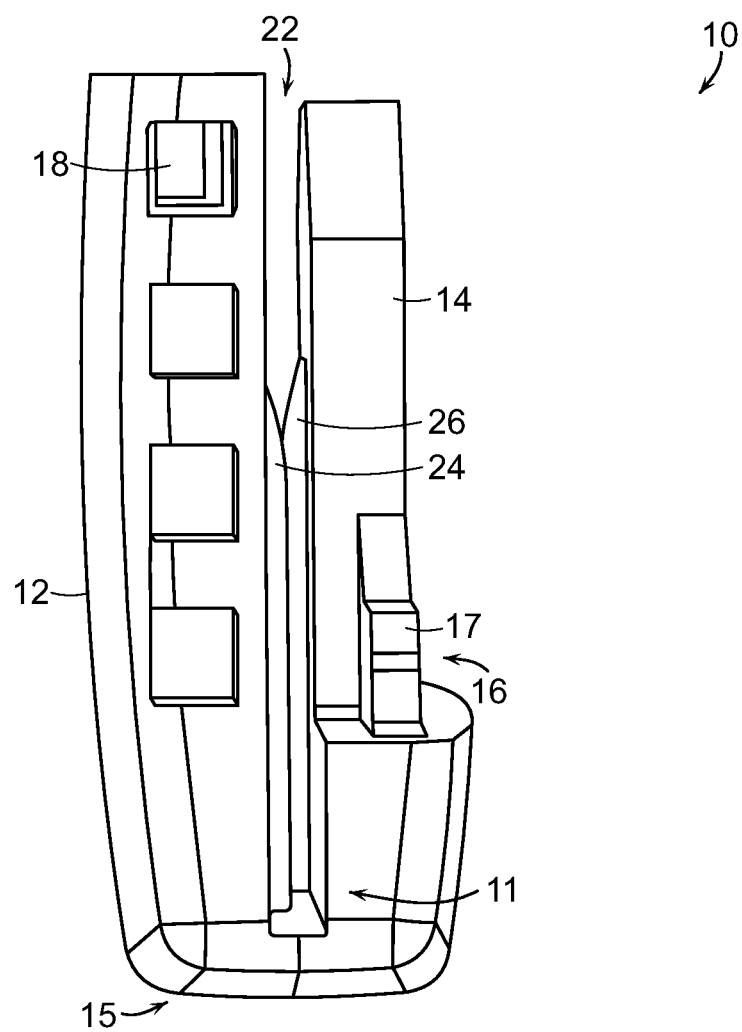
FIG. 1D is a side view of the interlocking member of FIGS. 1A through 1C, according an example embodiment of the inventive concepts.

FIGS. 1A through 1C are illustrative perspective views of an interlocking member, as one of two interlocking members used to form a clasp, according to an example embodiment of the inventive concepts. FIG. 1D is a side view of the interlocking member of FIGS. 1A through 1C, according an example embodiment of the inventive concepts.

Figure 2A:
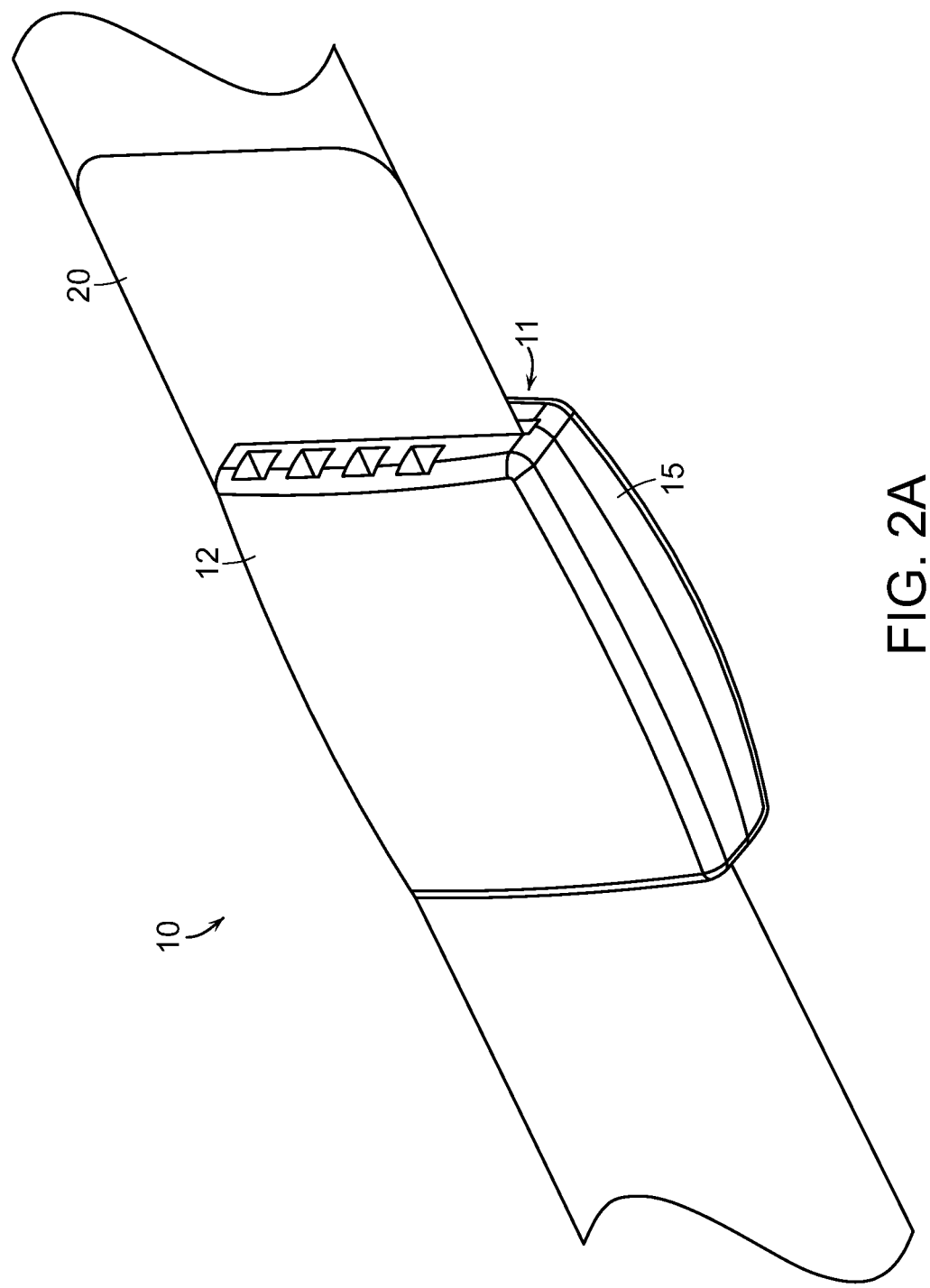
FIGS. 2A through 2C show different views of the interlocking member of FIGS. 1A-1D having a band disposed therein, according to an example embodiment of the inventive concepts.
Figure 2B:
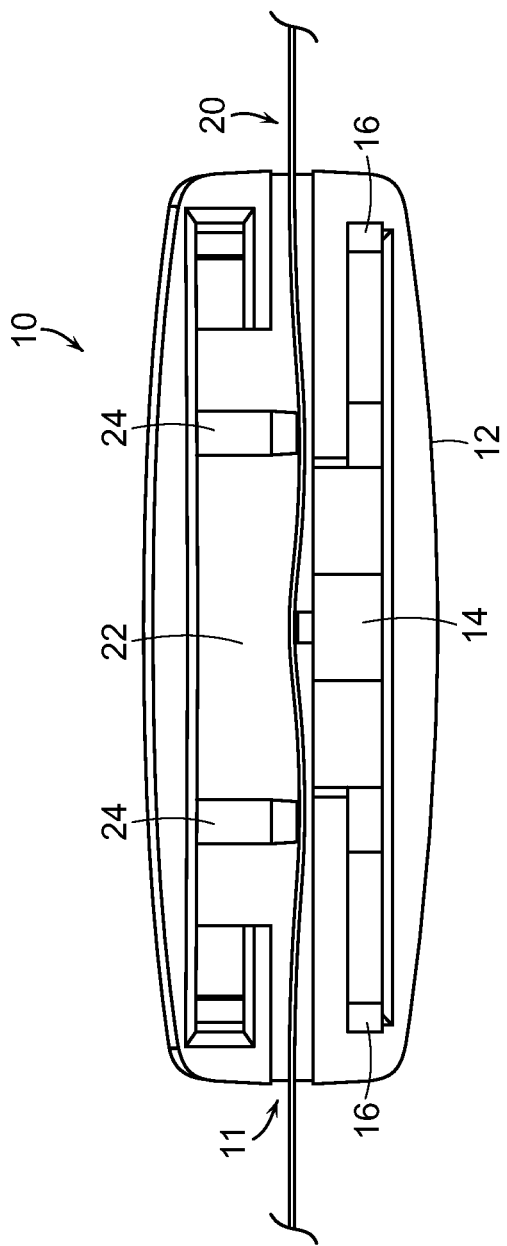
Figure 2C:
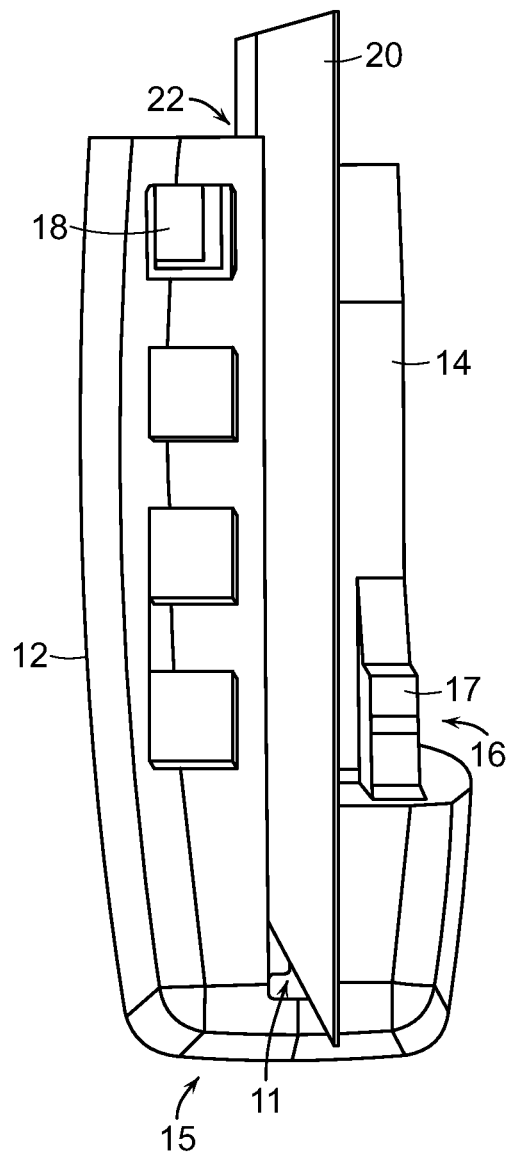

FIGS. 2A through 2C show different views of the interlocking member of FIGS. 1A-1D having a band disposed therein, according to an example embodiment of the inventive concepts. FIG. 2B shows a top view of the interlocking member of FIG. 2A and FIG. 2C shows a side view of the interlocking member of FIG. 2A, according to an example embodiment of the inventive concepts.

Figure 3B:
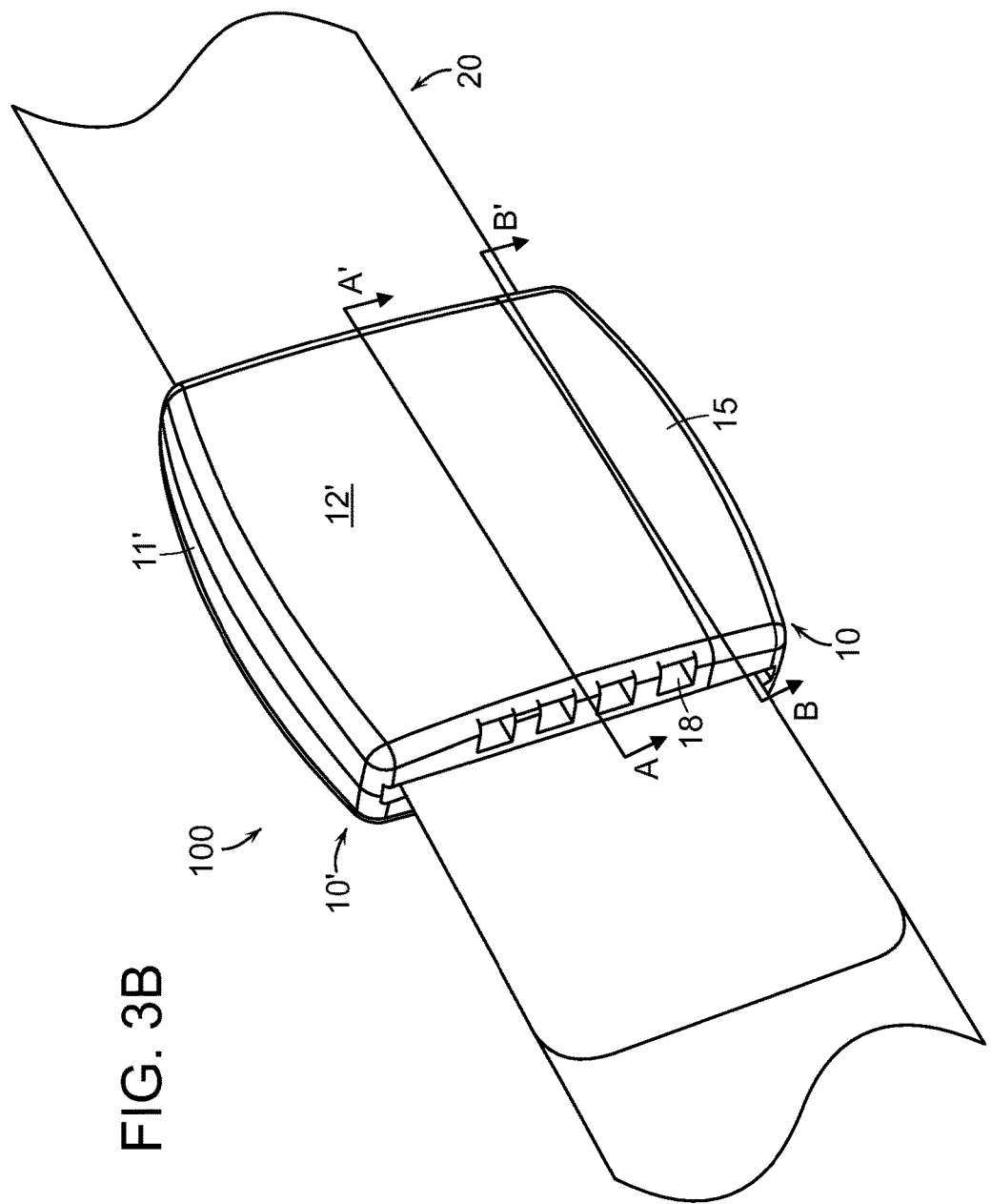
Figure 3D:
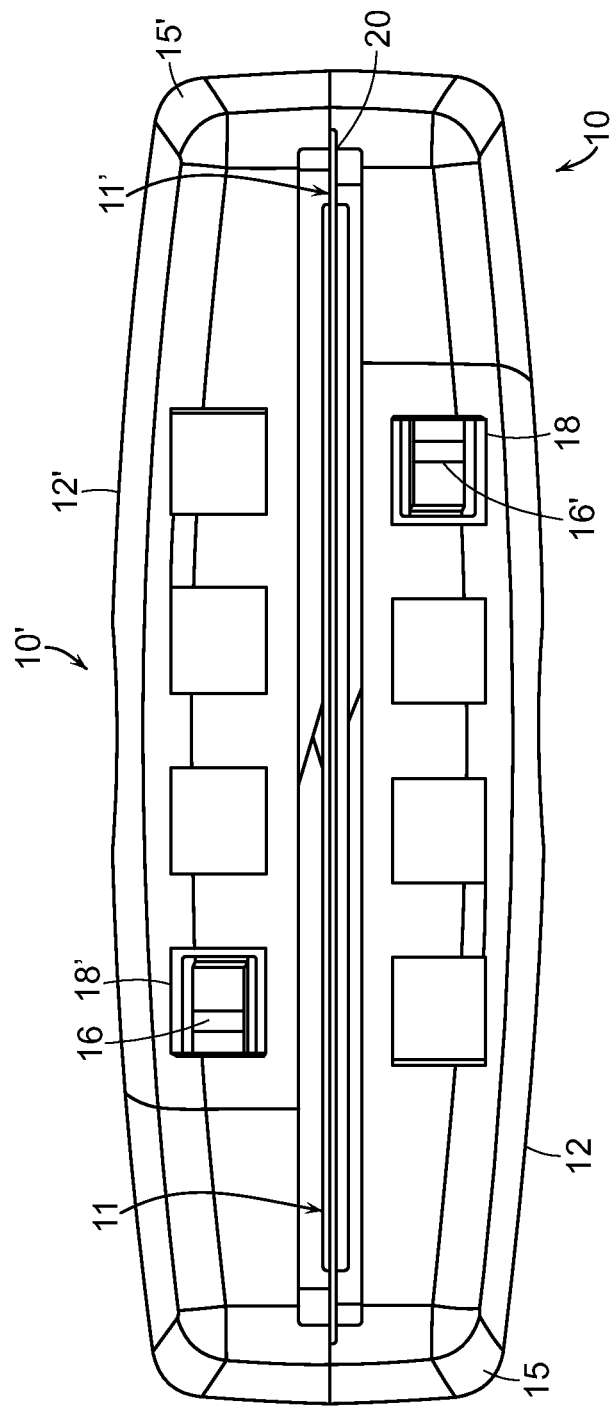
FIG. 3D is a side view of the clasp of FIG. 3A, according to an example embodiment of the present inventive concepts.
Figure 3E:
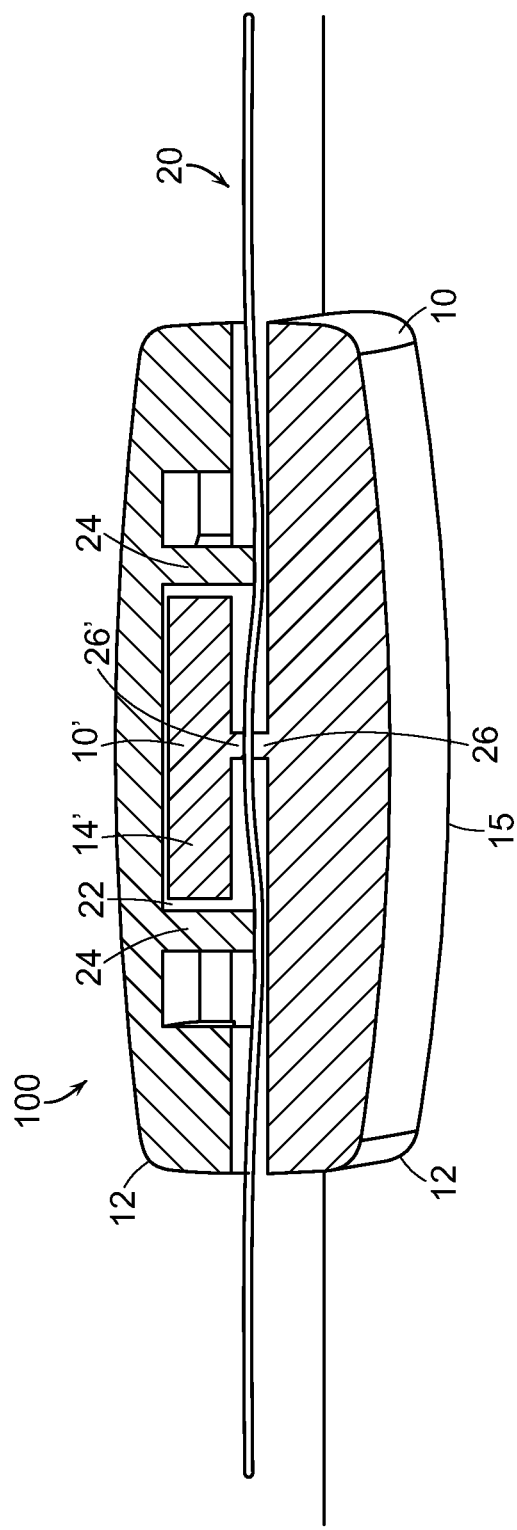
FIG. 3E is a cross-sectional perspective view of the clasp having a flexible band within the clasp of FIG. 3B taken along line B-B' at a different angle from FIG. 3C, according to an example embodiment of the present inventive concepts.

FIGS. 3A and 3B are illustrative perspective views of a clasp comprising two interlocking members, according to an example embodiment of the present inventive concepts. FIG. 3C is a cross-sectional perspective view of the clasp of FIG. 3B taken along line A-A', according to an example embodiment of the present inventive concepts. FIG. 3D is a side view of the clasp of FIG. 3A, according to an example embodiment of the present inventive concepts. FIG. 3E is a cross-sectional perspective view of the clasp having a flexible band within the clasp of FIG. 3B taken along line B-B' at a different angle from FIG. 3C, according to an example embodiment of the present inventive concepts.

FIGS. 1A-1C show an example embodiment of an interlocking member 10 that can be used as one of two interlocking members that combine to form a clasp 100 within which a flexible band 20 may be secured, see also FIGS. 3A-3E. In these embodiments, the two interlocking members used to form a clasp may be substantially the same, that is, two of the same piece. In various embodiments, the clasp may be structured to accommodate available 1" bands, but in other embodiments the clasp could be structured to fit ¾" and ½" bands, as examples. There are no inherent limitations on the scaling or uses of the clasp and bands.

A flexible band of material (or "flexible band", or "band") 20, for example, a strap or wrist band, may be waterproof, chemical resistant, and scratchproof. In addition, the band 20 may be stretch proof and tear proof so that it needs to be cut off to be removed. The band 20 may include at least one of a strip of cables, plastic, and fibers, as examples.

In the example embodiment, the clasp is arranged to enclose and prevent access to a closure region of the band 20. The closure region can be a seam or an area where two portions of a least one band overlap. In FIGS. 2A-2D, for example, the interlocking member 10 is shown with an overlapped area of two ends of flexible band 20 disposed therein.

The clasp includes first and second interlocking members 10. The first and second interlocking members 10 are identically formed pieces in this embodiment, but need not be in others. Each interlocking member 10 includes an outer shell 12 having interlocking recesses 18 formed therein. Each interlocking member 10 also includes a tongue 14 having outwardly projecting interlocking hooks 16 and a tongue receiving slot 22 formed between the tongue 14 and the outer shell 12.

In this embodiment, opposite tongue 14 there is an inner surface 23 of shell 12 forming a portion of the tongue receiving slot 22. The inner surface 23, as illustrated in FIGS. 1B and 1C, includes internal ribs 24 protruding from the inner surface 23 and forming opposing sides of the tongue receiving slot 22. In this embodiment, ribs 24 are spaced apart at a distance that is slightly greater than the width of the tongue 14 to be received in tongue receiving slot 22. Preferably, insertion of tongue 14 in tongue receiving slot 22 causes a tight fit of band 20 therein, that is, a fit that grips and compresses band 20 to render band 20 substantially immovable.

As illustrated in FIGS. 1C and 1D, the tongue 14 includes at least one protrusion 26 extending from a tongue back surface 13 and forming a portion of the tongue receiving slot 22. The protrusion 26 is configured to reduce or prevent sliding of the band 20 between the opposing interlocking members 10 when interlocked. In this embodiment, the protrusion 26 is centered in the rear of tongue 14 so that protrusions of two combined interlocking members compress band 20. But in other embodiments there may be more than one protrusion on one or both tongues of the two combined interlocking members, and the protrusion may not be centered. Each interlocking member 10 includes a base 15 from which the outer shell 12 and tongue 14 extend substantially in parallel. Within the base 15, a channel 11 is formed, at the bottom of the receiving slot 22.

In this embodiment, interlocking member 10 includes two interlocking hooks 16 and two interlocking recesses 18. In this embodiment, recesses 18 are shown as being open, creating a window through which hooks 16 can be seen when two interlocking members are combined. However, such a window is not essential, that is, recess 18 could be completely internal to the clasp and not externally visible. Each of the interlocking hooks 16 of a first interlocking member is arranged to engage and interlock with a corresponding one of the interlocking recesses 18 of a second interlocking member and each of the interlocking hooks 16 of the second member is arranged to interlock with one of the interlocking recesses 18 of the first interlocking member, so as to prevent movement between the interlocking members when interlocked. Therefore, the interlocking hooks 16 of each of the interlocking members 10 are configured to engage and snap into corresponding interlocking recesses 18 of the opposing interlocking member, securing and interlocking the two members with each other as shown in FIGS. 2A and 3A.

In the preferred embodiment, the interlocking hooks 16 are not spring-loaded or otherwise displaceable so that the interlocking members 10 are not releasable once engaged, even with a tool. As illustrated in FIGS. 1A through 1D, each of the interlocking hooks 16 includes an angled member 17 configured to facilitate insertion into a corresponding interlocking recess 18 and a stop member 19 configured to prohibit removal of the interlocking hook from the corresponding interlocking recess, see, for example, FIG. 3C.

As illustrated in FIGS. 2A through 2C, the first interlocking member 10 is shown with the flexible band 20 disposed between the tongue 14 and internal ribs 24 of the first interlocking member 10.

In an example embodiment, as illustrated in FIGS. 2B and 3E, a portion of the band 20 is positioned within the interlocking member 10 within channel 11. As such, band 20 passes by and contacts the tongue 14, opposing internal ribs 24 and protrusions 26 in a serpentine-like manner. The primary cause for this manner of the shape of band 20 within channel 11 is that protrusion 26 extends from tongue 14 partially in to the channel 11, as do ribs 24 on the opposite side of channel 11. As a result, a straight line path through the channel 11 does not exist for band 20, which bends around protrusions 26 and internal ribs 24 when disposed in channel 11. Accordingly, the band 20 is held in place when two interlocking members are combined, which substantially prevents the band 20 from sliding through the clasp. The serpentine-like manner of the band 20 prevents the band 20 from sliding in the left and right directions within the clasp As illustrated in FIG. 3B, the clasp includes relatively smooth surfaces with rounded edges so as to improve comfort to an individual wearing the strap/clasp and to help avoid injury from the clasp while being worn.

Referring to FIGS. 3A-3E, a clasp 100 is shown formed of two interlocking members 10, 10', having band 20 secured therein.

In various embodiments, the clasp 100 may be constructed of plastic, resin, metal, or similar materials. In various embodiments, the clasp may be molded of or generated from a single material that is sufficiently flexible to permit the interlocking hooks 16 to flex/snap/engage into the interlocking recesses 18, while being strong enough to prevent easy breakage or removal of the clasp 100. In an various embodiments, the clasp 100 may be constructed of Acrylonitrile Butadiene Styrene (ABS). Depending on the intended use, a softer plastic with characteristics similar to that of Poly Olefins, for example, would be avoided with respect to at least the outer protective shell of the clasp, that is, in cases where the clasp functions as a secure device.

The clasp 100 of the example of embodiments of the present inventive concepts includes two substantially identical interlocking members 10, 10' which may be put together with the force of a hand, but do not come apart. In addition, the clasp 100 engages the band 20 in such a manner that no holes or rivets are produced in the band which could weaken the band. The clasp 100 includes four attachment points which substantially prevent movement between the interlocking members when interlocked. The clasp 100 includes interlocking hooks 16, 16' which are not spring-loaded so that the interlocking members are not releasable once engaged, even with a tool, see, for example, FIG. 3A. The clasp 100 has smooth edges, that is, no sharp edges, so that the clasp cannot be turned into a weapon.

When the first and second interlocking members 10, 10' are interlocked or engaged, the tongue 14 of one interlocking member 10 fits within the tongue receiving slot 22' of the other interlocking member 10' and the hooks 16 of one interlocking member 10 engage the interlocking recesses 18' of the other interlocking member 10', so as to prevent disengagement of the interlocking members 10, 10'. When the first and second interlocking members 10, 10' are interlocked, a portion of the band 20 is disposed between and in parallel with the tongues and the outer shells 12, 12' of the first and second interlocking members 10, 10'.

FIG. 3A demonstrates how first and second interlocking members 10, 10' combine to form clasp 100, in accordance with the example embodiment. The band 20 is disposed in channel 11 of first interlocking member 10, then second interlocking member 10' is placed over band 20 such that tongue 14 of first interlocking member 10 inserts into tongue receiving slot 22' of the second interlocking member 10' and tongue 14' of the second interlocking member 10' inserts into tongue receiving slot 22 of the first interlocking member 10. As the two interlocking members are pressed together, hooks 16 of the first interlocking member 10 are irremovably forced into the corresponding recesses 18' of the second interlocking member 10' and hooks 16' of the second interlocking member 10' are irremovably forced into recesses 18 of the first interlocking member 10, as is shown in the side view of FIG. 3D.

FIG. 3B shows the interlocking members 10, 10' combined to form clasp 100 and FIG. 3C shows a cross-section of clasp 100 taken alone line A-A' of FIG. 3B. In FIG. 3C band 20 is engaged and compressed between protrusions 26, 26' of the first and second interlocking members 10, 10', respectively. Similarly, band 20 may also be compressed between opposing ribs 24, 24' of first and second interlocking members 10, 10', respectively.

FIG. 3E is a cross-sectional perspective view of clasp 100 having flexible band 20 secured therein, taken along line B-B' in FIG. 3B. As is shown in FIG. 3E, band 20 is secured in a serpentine-like path through clasp 100, similar to what is shown in FIG. 2B. As is apparent from FIG. 3E, near the base 15 of interlocking member 10, tongue 14' of interlocking member 10' is pushed toward the outside of receiving slot 22 from the force of the more rigid base 15 (from which tongue 14 extends) applied to a distal end of tongue 14'. Thus, the serpentine-like bending of band 20 shown in FIG. 2B is maintained when interlocking members 10, 10' are combined. The same aspects would be realized at base 15' (not shown) of interlocking member 10'. Similarly, base 15' would push tongue 14 toward the outside of receiving slot 22', when band 20 is compressed between the interlocking members 10,10'. Therefore, in this embodiment, the serpentine-like bending of band 20 at base 15' of interlocking member 10' would be opposite that shown for base 15 of interlocking member 10.

In other embodiments, the clasp may include other types of devices and/or sensors embedded therein, for example, a RFID chip, wander sensors, medical monitoring devices and GPS tracking devices. The interlocking members that form such a clasp may be as otherwise described above, that is, with respect to FIGS. 1A-1D, 2A-2C, and 3A-3E.

Figure 4A:
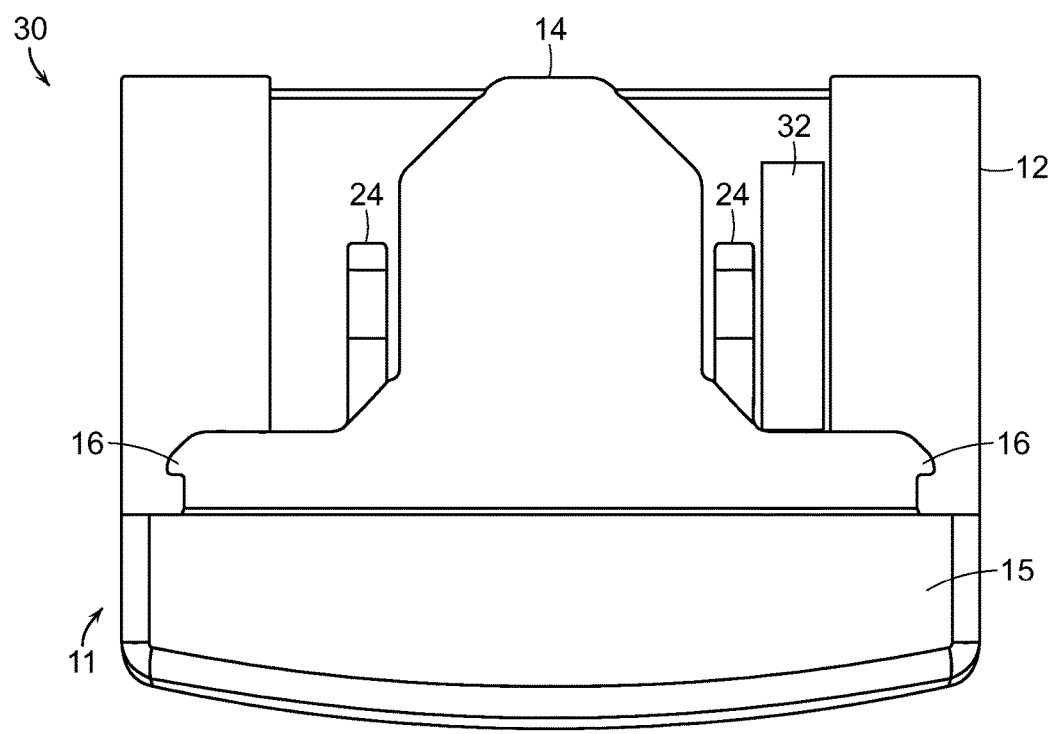
FIGS. 4A and 5A are illustrative front views of an interlocking member of a clasp having a passive radio frequency identification (RFID) chip, according to an example embodiment of the inventive concepts.
Figure 4B:
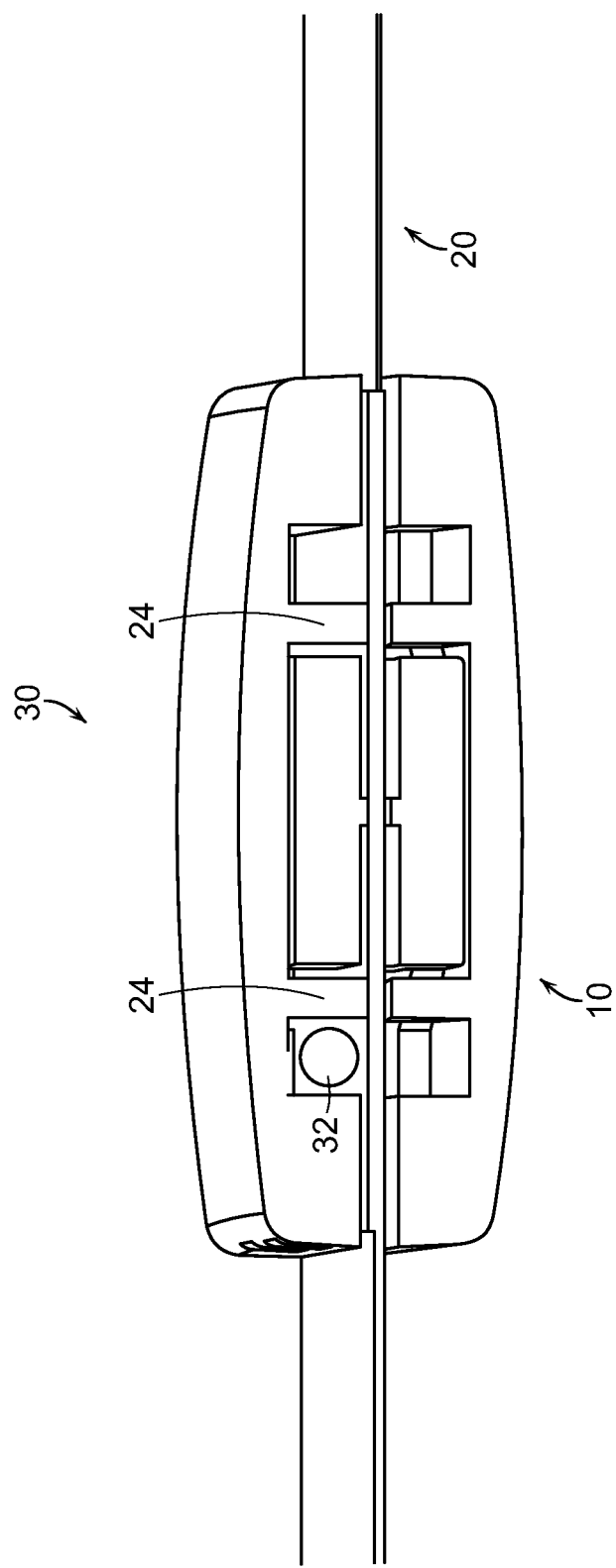
FIGS. 4B and 5B are cross-sectional perspective views of the interlocking members of FIGS. 4A and 5A forming part of a clasp that is cut along line A-A' as in FIG. 3A, respectively, according to an example embodiment of the inventive concepts.
Figure 5A:
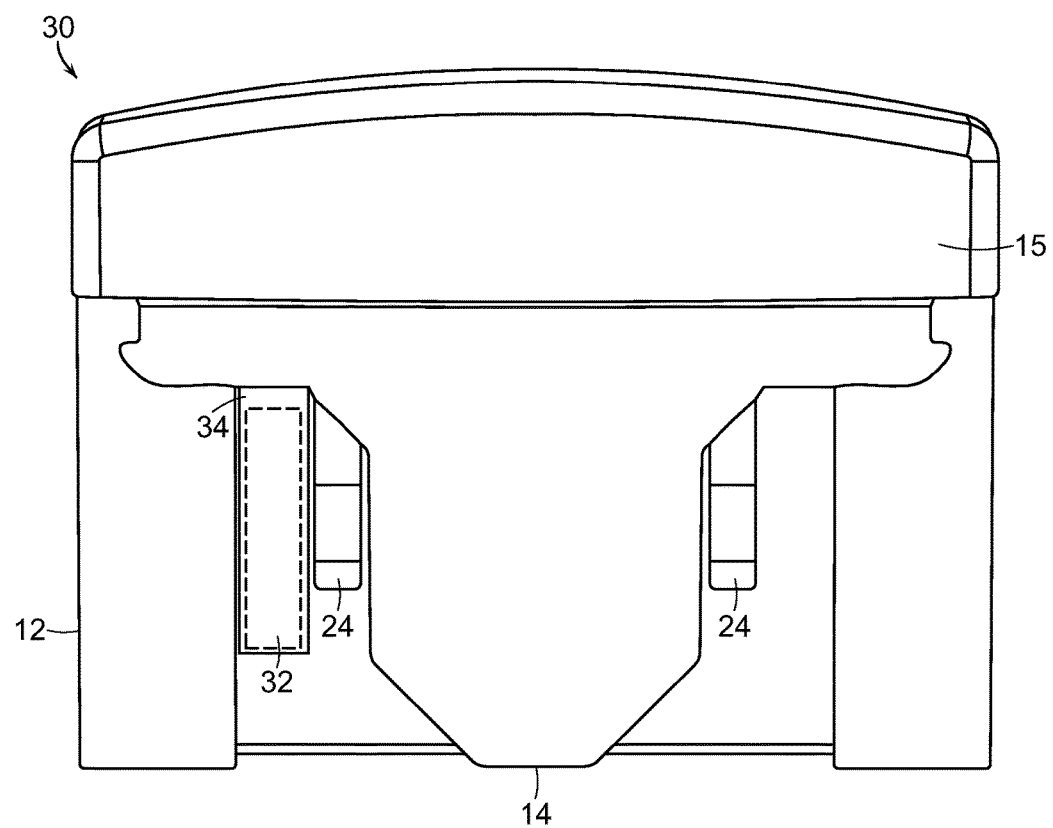
Figure 5B:
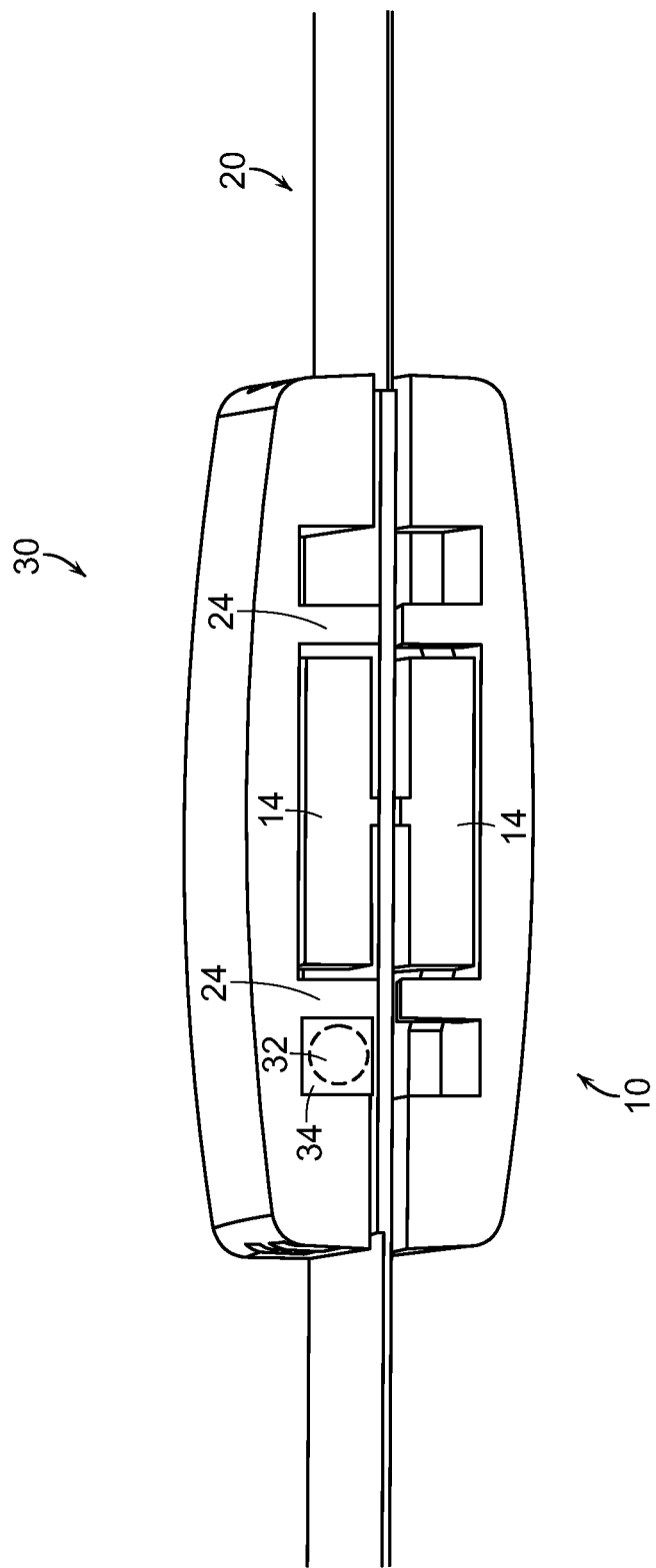

FIGS. 4A and 5A are illustrative perspective views of an interlocking member of a clasp having a passive radio frequency identification (RFID) chip, according to an example embodiment of the inventive concepts. FIGS. 4B and 5B are cross-sectional perspective views of the interlocking members of FIGS. 4A and 4A forming part of a clasp that is cut along line A-A' as in FIG. 3A, respectively, according to an example embodiment of the inventive concepts.

In FIGS. 4A and 5A, the interlocking members 30 are similar to the interlocking members 10, 10', as discussed above. The interlocking members 30 of FIGS. 4A, 4B, 5A and 5B further include a passive RFID chip 32. The passive RFID chip 32 relies entirely on a reader of the RFID chip as its power source, in this embodiment.

In FIGS. 4A and 4B, the RFID chip 32 may be coupled to the interlocking member 30 by adhesive, such as glue. In FIGS. 5A and 5B, a pocket 34 is molded onto the interlocking member 30 between one of the internal ribs 24 and the outer shell 12 and the RFID chip 32 is inserted therein.

In FIGS. 4A, 4B, 5A and 5B, the RFID chip 32 is located between one of the internal ribs 24 and the outer shell 12. In FIGS. 4A and 4B, the RFID chip 32 is located between the inner surface 23 and a surface of the internal ribs 24 which interfaces with the band 20. In FIGS. 5A and 5B, the pocket 34 is located between the inner surface 23 and a surface of the internal ribs 24 which interfaces with the band 20.

Figure 6A:
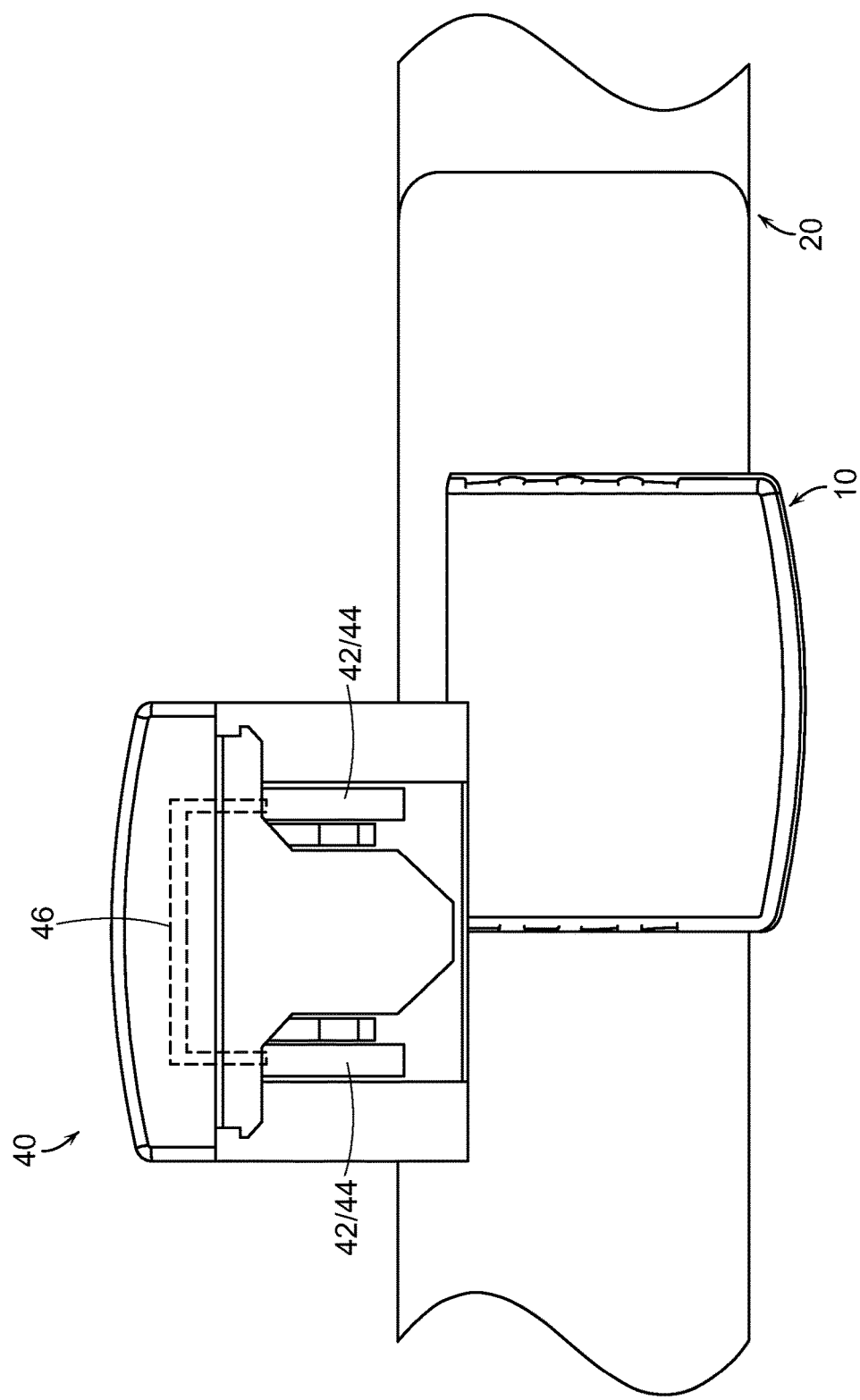
Figure 6B:
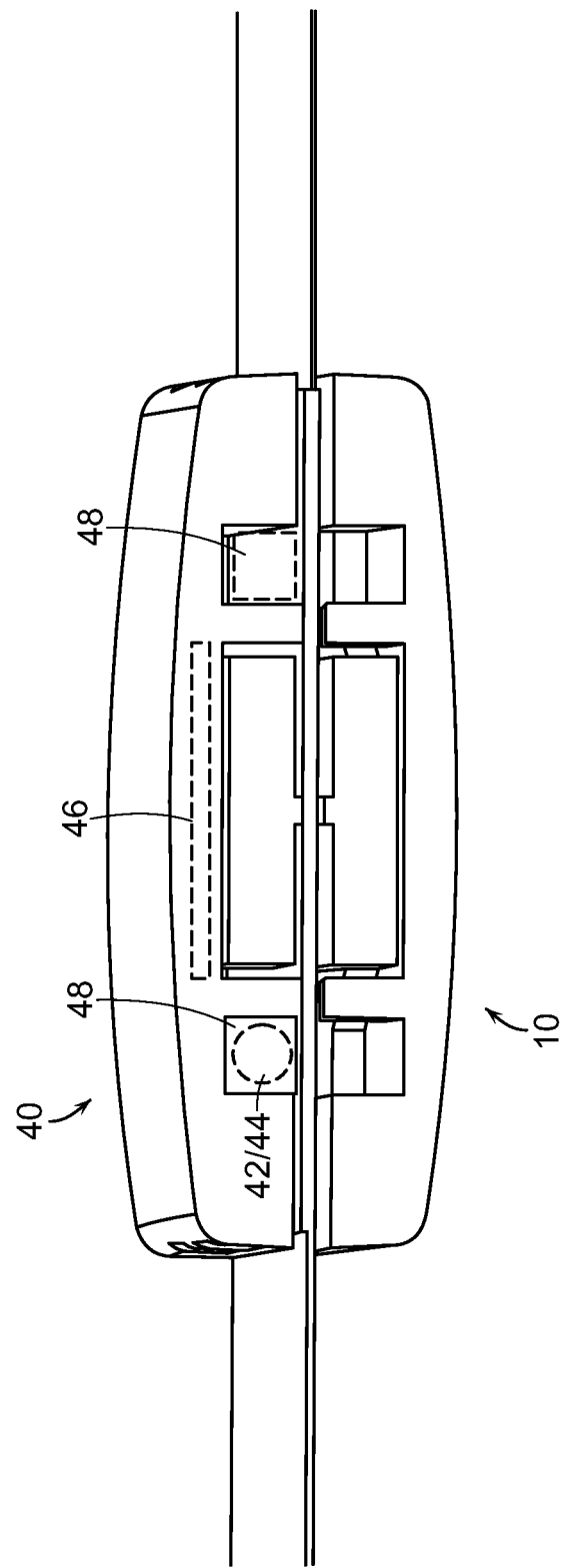

FIGS. 6A and 7A are illustrative perspective views of two interlocking members of a clasp having an active RFID chip, according to an example embodiment of the inventive concepts. FIGS. 6B and 7B are cross-sectional perspective views of the interlocking members of FIGS. 6A and 7A, respectively forming part of a clasp that is cut along line A-A' as in FIG. 3A, respectively, according to an example embodiment of the inventive concepts. Active RFID chips use internal batteries to power their circuits, in this embodiment.

FIGS. 6A and 6B illustrate both an active RFID chip 42 and a battery 44 being formed on a single side of a clasp 40. That is, the active RFID chip 42 and the battery 44 are only formed on one of the interlocking members of the clasp, namely clasp 40. The active RFID chip 42 and the battery 44 are coupled by circuitry 46. Pockets 48 are molded onto the interlocking member 40 between each of the internal ribs 24 and the outer shell 12 and the RFID chip 42 and the battery are inserted therein, respectively. In FIGS. 6A and 6B, the pockets 48 are located between the inner surface 23 and a surface of the internal ribs 24 which interfaces with the band 20.

A switch is formed on an external face of the interlocking member such that the active RFID chip 42 is activated when the interlocking members are engaged or interlocked. In an alternative embodiment, the active RFID chip 42 is activated prior to the interlocking members being engaged or interlocked.

FIGS. 7A and 7B illustrate an active RFID chip 54 being formed on one of the interlocking members of the clasp, namely, interlocking member 50, and a battery 60 being formed on the other of the interlocking members of the clasp, namely, interlocking member 52. The active RFID chip 54 is coupled to an exposed contact 58 by circuitry 56. The exposed contact 58 is on the tongue 14 of the interlocking member 50. In an example embodiment, the contact 58 is formed on the top of the tongue 14.

The battery 60 is inserted or molded into the plastic or other material of the interlocking member 52. In one example embodiment, the battery 60 is formed on the inner surface 23 of the interlocking member 52. In one example embodiment, the battery 60 is disk-shaped; however, the present inventive concepts are not limited thereto. The battery 60 has an exposed contact thereon.

The exposed contact 58 on the tongue 14 will come in contact with the underside of the exposed contact on the battery 60 when the clasp is closed thereby activating the active RFID chip.

While the inventive concepts have been particularly shown and described with references to example embodiments thereof, it will be understood to those skilled in the art that various changes in form and details may be made herein without departing from the spirit and scope of the invention as defined in the appended claims.

What is claimed is:

1. A clasp configured to permanently secure a flexible band, comprising:
   first and second interlocking members, each interlocking member comprising: a shell; a tongue;
   a base from which the shell and the tongue extend substantially in parallel; and
   a positive interlocking mechanism and a negative interlocking mechanism, wherein, when interlocked, the positive and negative interlocking mechanisms of the first and second interlocking members permanently interlock to form the clasp having a first opening, a second opening opposite the first opening, and a path extending through the clasp between the first and second openings for pass through of a flexible band permanently secured by compression between the tongues of the first and second interlocking members, wherein each tongue further comprises at least one protrusion extending from a back surface of the tongue toward the shell.

2. The clasp of claim 1, wherein a tongue receiving slot is defined between the tongue and the shell of each of the first and second interlocking members, wherein each tongue receiving slot is constructed to receive the tongue of the other interlocking member.

3. The clasp of claim 1, wherein the first and second openings extend in a direction parallel to the tongues of the first and second interlocking members.

4. The clasp of claim 1, wherein the flexible band is disposed in parallel with the shell and tongue of each interlocking member when the flexible band is secured in the clasp.

5. The clasp of claim 1, wherein, when interlocked, the protrusions of tongues of the first and second interlocking members compress and secure the flexible band therebetween.

6. The clasp of claim 5, wherein the path is an internal serpentine path formed between the protrusions of the tongues.

7. The clasp of claim 1, wherein the first and second interlocking members are identical.

8. The clasp of claim 1, wherein:
   the positive interlocking mechanism comprises two interlocking hooks;
   the negative interlocking mechanism comprises two interlocking recesses configured to permanently receive the two interlocking hooks of the other interlocking member.

9. The clasp of claim 8, wherein:
   the two interlocking hooks are outwardly projecting protrusions of the tongue; and
   the two interlocking recesses are formed on outer portions of the shell proximal to the first and second openings, respectively.

10. The clasp of claim 8, wherein each interlocking hook comprises an angled side configured to facilitate insertion into a corresponding interlocking recess and a stop side configured to prohibit removal of the interlocking hook from the corresponding interlocking recess.

11. The clasp of claim 1, wherein each shell comprises:
    an inner surface opposite the tongue and forming a portion of the tongue receiving slot; and
    at least one rib extending from the inner surface toward and in parallel with the tongue and into the tongue receiving slot.

12. The clasp of claim 1, wherein each shell comprises two ribs forming guides arranged to slidably receive therebetween the tongue of the other interlocking member.

13. The clasp of claim 1, wherein the flexible band is a flexible wristband.

14. The clasp of claim 1, wherein the flexible band is a flexible identification band.

15. The clasp of claim 1, wherein the flexible band comprises at least one of a strip of cables, plastic, and fibers.

16. The clasp of claim 1, wherein the clasp is constructed substantially of at least one of plastic, resin, and metal.

17. The clasp of claim 1, wherein at least one of the first and second interlocking members comprises a radio frequency identification (RFID) chip.

18. A clasp configured to permanently secure a flexible band, comprising:
    first and second interlocking members, each interlocking member comprising:
    a shell;
    a tongue;
    a base from which the shell and the tongue extend substantially in parallel;
    a tongue receiving slot defined between the tongue and the shell, the tongue receiving slot constructed to receive the tongue of the other interlocking member; and
    a positive interlocking mechanism and a negative interlocking mechanism,
    wherein, when interlocked, the positive and negative interlocking mechanisms of the first and second interlocking members permanently interlock to form the clasp having a first opening, a second opening opposite the first opening, and a path extending through the clasp between the first and second openings for pass through of a flexible band permanently secured by compression between the tongues of the first and second interlocking members,
    wherein each tongue further comprises at least one protrusion extending from a back surface of the tongue into the tongue receiving slot, and when interlocked, the protrusions of tongues of the first and second interlocking members compress and secure the flexible band therebetween.

19. The clasp of claim 18, wherein the flexible band is a flexible identification band and the clasp is configured to permanently secure overlapping portions of the flexible band.

* * * * *